US005954642A

United States Patent [19]
Johnson et al.

[11] Patent Number: 5,954,642
[45] Date of Patent: Sep. 21, 1999

[54] ADJUSTABLE HEAD MOUNTED DISPLAY AND SYSTEM

[75] Inventors: Brett R. Johnson, St. Paul; Scott A. Nelson, Eagan; Jeff E. Madison, Oakdale, all of Minn.; Phil C. Dretzka, Cleveland Heights, Ohio

[73] Assignee: Honeywell Inc., Minneapolis, Minn.

[21] Appl. No.: 08/996,707

[22] Filed: Dec. 23, 1997

[51] Int. Cl.[6] ................................................. A61N 19/00
[52] U.S. Cl. ............................................................ 600/300
[58] Field of Search .............................. 600/300; 128/897

[56] References Cited

U.S. PATENT DOCUMENTS

| | | |
|---|---|---|
| 2,426,958 | 9/1947 | Ullett, Jr. et al. ....................... 600/383 |
| 4,310,849 | 1/1982 | Glass . |
| 4,449,787 | 5/1984 | Burbo et al. ................................ 345/8 |
| 4,559,555 | 12/1985 | Schoolman . |
| 4,636,866 | 1/1987 | Hattori . |
| 4,706,117 | 11/1987 | Schoolman . |
| 4,737,972 | 4/1988 | Schoolman . |
| 5,003,300 | 3/1991 | Wells . |
| 5,208,449 | 5/1993 | Eastman et al. . |
| 5,281,957 | 1/1994 | Schoolman . |
| 5,450,596 | 9/1995 | Felsenstein . |
| 5,746,693 | 5/1998 | Spitz et al. ............................... 600/160 |
| 5,767,820 | 6/1998 | Bassett et al. ............................... 345/8 |

OTHER PUBLICATIONS

Product Literature, "The ProView™ 30 Head Mounted Display System", Kaiser Electro–Optics Laser, Inc., 4 pgs., (available at least in Apr. 1997).
C. Murray, "Head–Mounted Display Simplifies Surgery", *Design News*, pp. 102–103, Aug. 11, 1997.
Product Literature, "Advanced Flat Panel Head Mounted Display Program", *R&D Programs, Electronics Technology Office*, http://esto.sysplan.com,2pgs., (accessed via internet Apr. 1997)(last updated Apr. 1996).
Product Literature, "HIDEF Family", *KEO*, http://www.keo.com,2 pgs., (accessed via internet Apr. 1997).
Product Literature, "Kaiser Electro–Optics", *KEO*, http://www.keo.com,4 pgs., (accessed via internet Apr. 1997)(copyright 1997).
Product Literature, "Full Immersion Head Mounted Display (FIHMD)", *ISO Planning & C3 Program Portfolio*, http://maco.dc.isx.com, 2pgs., (accessed via internet Apr. 1997).
Product Literature, "Head Mounted Display", http://ece.clemson.edu, 1 pg., (accessed via internet Apr. 1997).
Product Literature, "Head Mounted Displays (HMD)", *R&D Programs, Electronics Technology Office*, http://esto.sysplan.com, 3pp., (accessed via internet Apr. 1997).
Product Literature, *Intervision*, http://www.intervisionsystems.com, 6pgs., (accessed via internet May 1997)(copyright 1995, 1996).
Product Literature, "Look Past Today With Trekker™", *Personal Information Systems*, http://www.cacd.rockwell.com, 4pgs., (accessed via internet May 1997)(copyright 1996).

(List continued on next page.)

*Primary Examiner*—William E. Kamm
*Attorney, Agent, or Firm*—Ian D. Mackinnon

[57] ABSTRACT

A head mounted display includes a head suspension apparatus and a display coupled thereto. In a stationary state, the display is maintained in a desired position relative to the head suspension apparatus. Further, in a release state, the display is always freely movable both vertically and horizontally relative to the head suspension apparatus. In addition, the display may also always be freely rotatable about an axis of the display as well as vertically and horizontally. The coupling of the display to the head suspension apparatus may be attained using a slide bar and hinge mechanism that forms a rigid triangular structure when the display is in the stationary state. Further, the head suspension apparatus may include an adjustable temporal support element for positioning about the circumference of a user's head and an adjustable crown support connected to the temporal support with the crown support including channels for allowing electrical connection lines to move freely therein.

20 Claims, 11 Drawing Sheets

OTHER PUBLICATIONS

Product Literature, "Boeing Wearable Computer Workshop Breakout Session Summary", *Boeing Wearable Computer Workshop,* http://www.cs.smu.edu, 3pgs., (accessed via internet May 1997).

Product Literature, "The MIT Wearable Computing Page", http://lcs.www.media.mit.edu, 5 pgs., (accessed via internet May 1997).

Product Literature, "Wearable Computing Research Group", *University of Oregon Computer & Information Science,* http://www.cs.uoregon.edu, 2pgs., (accessed via internet May 1997)(last updated Jan. 1997).

Product Literature, "Electronic Performance Support System", *EPSS,* http://mime1.marc.gatech.edu, 6 pgs., (accessed via internet May 1997)(last updated Apr. 1997).

Product Literature, "Shape Deposition Manufacturing", http://www-rpl.stanford.edu, 2 pgs., (accessed via internet May 1997).

Product Literature, "The DeVry Student Chapter I.E.E.E. Official Wearable Computer Homepage", http://www.devry-cols.edu, 3 pgs., (accessed via internet May 1997)(copyright 1997).

Product Literature, "*Jeff Hartman's Wearable Computer Technical page:*", http://www.netwalk,com, 2 pgs., (accessed via internet Apr. 1997)(Last updated Jan. 1997)(copyright 1996).

Product Literature, "The Ultimate Portable Computer?", *News & Views,* Copyright 1994–1997, http://www.byte.com, 2 pgs., (accessed via internet Apr. 1997)(copyright 1994–1997).

ADJUSTABLE HEAD MOUNTED DISPLAY AND SYSTEM

GOVERNMENT LICENSE RIGHTS

The present invention was made with U.S. Government support under Contract No. DAAK60-94-C-0040 awarded by the U.S. Army NATICK R&D Center on May 27, 1994. The U.S. Government has certain rights in the invention.

FIELD OF THE INVENTION

The present invention relates to head mounted displays. More particularly, the present invention pertains to adjustable head mounted displays wherein the display is movable relative to the eyes of the user.

BACKGROUND OF THE INVENTION

Various head mounted displays are available. Users of head mounted displays have different requirements depending upon the application. For example, users of head mounted displays for remote conferencing, industrial processing, and surgical procedures will each have different requirements for the head mounted displays. Further, within a particular application, such as surgical procedure applications for head mounted displays, users also have different requirements or different needs. For example, in surgical procedures, head mounted displays must be adjustable with respect to the user's eyes, provide easy and fatigue-free viewing, provide dimensional viewing compatible with sensors (e.g., two dimensional and three dimensional viewing), limit interference with the surgeon's capability to perform surgery, etc.

One head mounted display available from Kaiser Electro-Optics, Inc. (Carlsbad, Calif.) under the trade designation ProView™, provides various adjustments to adapt the head mounted display to a wide variety of users and applications. For example, Kaiser Electro-Optics displays provide inter-pupillary distance adjustment to allow the viewing modules or image sources to be properly adjusted to accommodate a wide range of viewers or users. Further, a height adjustment feature on the head mounted display allows positioning of the viewing modules or image sources for viewing. In addition, a horizontal adjustment allows the user to change the distance between the eyes of the user and the image sources or viewing modules so as to accommodate eyeglasses or safety glasses. Further, such adjustable head mounted displays include a tilt feature which allows the image source or viewing module to be rotated or tilted relative to the eyes such that the user can look up at the display or view the image source and keep the eyes on the particular work being performed. In addition, such tilt adjustment allows the user to flip the entire image source up and out of the way if the user wishes to take a break from work or viewing of the image source.

However, such currently available head mounted displays, including the Kaiser Electro-Optics displays, have associated drawbacks. For example, such head mounted displays require multiple adjustment mechanisms and multiple steps for adjusting the display or viewing modules relative to the user's eyes to achieve desired positioning of the image modules or sources for the user's applications. This is particularly problematic in applications where adjustment of the position of the image sources relative to the eyes of the user are to be performed as quickly and easily as possible with little interruption to the user.

For example, in a surgical application the user may need to adjust the position of a viewing module or image source as surgical procedures are being performed. Such adjustment may need to be made by an assistant at the surgical site as opposed to the user who is wearing the head mounted display so as to keep the surgical site sterile. Further, such adjustments during the surgical procedures must be made quickly to minimize interruption to the user's surgical procedure. The adjustments must also be intuitive to the user, e.g., unnecessary training to accomplish such adjustments must be minimized and/or the adjustment procedure must not be complicated. Likewise, head mounted displays used for such applications should have an open field of view to the user. For example, the position of cabling relative to the viewing modules for providing video signal thereto should minimize interruption in the field of view and also prevent any cable from snagging on other equipment in the surgical field. Conventional head mounted displays typically have service loops associated with the cabling, such as cabling which is provided to the rear of the user's head from the image modules through temporal supports of the headband suspending the display. Such service loops may interrupt the user's field of view and may snag on equipment in the surgical field.

SUMMARY OF THE INVENTION

The present invention, as described below, overcomes the problems described above and other problems which will become apparent to one skilled in the art from the description below. Generally, the present invention provides a head mounted display having a single point release adjustment mechanism for intuitive user positioning of the display relative to the user's eyes or, in other words, relative to the headband suspending the display in front of the user's head.

A head mounted display according to the present invention includes a head suspension apparatus. A display is coupled to the head suspension apparatus. In a stationary state, the display is maintained in a desired position relative to the head suspension apparatus. Further, in a release state, the display is always freely movable both vertically and horizontally relative to the head suspension apparatus.

In one embodiment of the head mounted display, the display includes an axis associated therewith. In the release state, the display is always freely rotatable about the axis as well as movable vertically and horizontally.

Another head mounted display according to the present invention includes a head suspension apparatus and a display. A coupling attaches the display to the head suspension apparatus. In a release state the coupling allows for movement of the display in both a horizontal and vertical direction relative to the head suspension apparatus and in a stationary state the display is locked in a position relative to the head suspension apparatus. The display includes a locking mechanism for normally maintaining the display in the stationary state. Further, the display includes a user actuator element operably coupled to the locking mechanism for releasing the display from the normally stationary state to the release state.

In one embodiment of the head mounted display, the display is also rotatable about an axis of the display in the release state.

In another embodiment of the head mounted display, the coupling includes a slide bar and hinge mechanism that forms a rigid triangular structure when the display is in the stationary state.

In another embodiment of the head mounted display, the slide bar and hinge mechanism includes two fixed hinge points and a movable hinge point.

In yet another embodiment of the head mounted display, the slide bar and hinge mechanism includes a first rigid member projecting from the head suspension apparatus, a second member having a first end rotatably coupled at a first fixed hinge point of the first rigid member and a second end including a slot slidingly coupled to a shaft element lying along an axis of the display, and a third member having a first end rotatably coupled at a second fixed hinge point of the first rigid member and a second end including a slot slidingly coupled to the shaft element.

In yet further another embodiment of the head mounted display, the locking mechanism and user actuator element are a clutch mechanism for disengaging and engaging a locking structure thereof relative to the coupling.

Another head mounted display according to the present invention includes a display having one or more image sources and a head suspension apparatus coupled to the display. The head suspension apparatus includes an adjustable temporal support element for positioning about the circumference of a user's head and an adjustable crown support having a first end connected to a first portion of the temporal support at the front of the user's head and a second end connected to a second portion of the temporal support at the rear of the user's head. The crown support includes one or more channels for allowing electrical connection lines to move freely therein. The electrical connection lines are routed in the channels from the one or more image sources to the rear of the user's head.

In various embodiments of the head mounted display, the head suspension apparatus includes a locking support portion at the rear of the user's head for use in locking the head suspension apparatus on the user's head, includes a crown adjustment element and a temporal adjustment element at the rear of the head for use in adjusting the size of the crown support and the size of the temporal support, and/or the crown support and the temporal support are formed of several pliable layers with the plurality of pliable layers increasing in rigidity from a pliable inner layer proximate the head to a pliable outer layer (e.g., the pliable outer layer may be slidable relative to one of the other layers as the head mounted display is adjusted to fit the user).

DETAILED DESCRIPTION OF THE EMBODIMENTS

Figure 1:
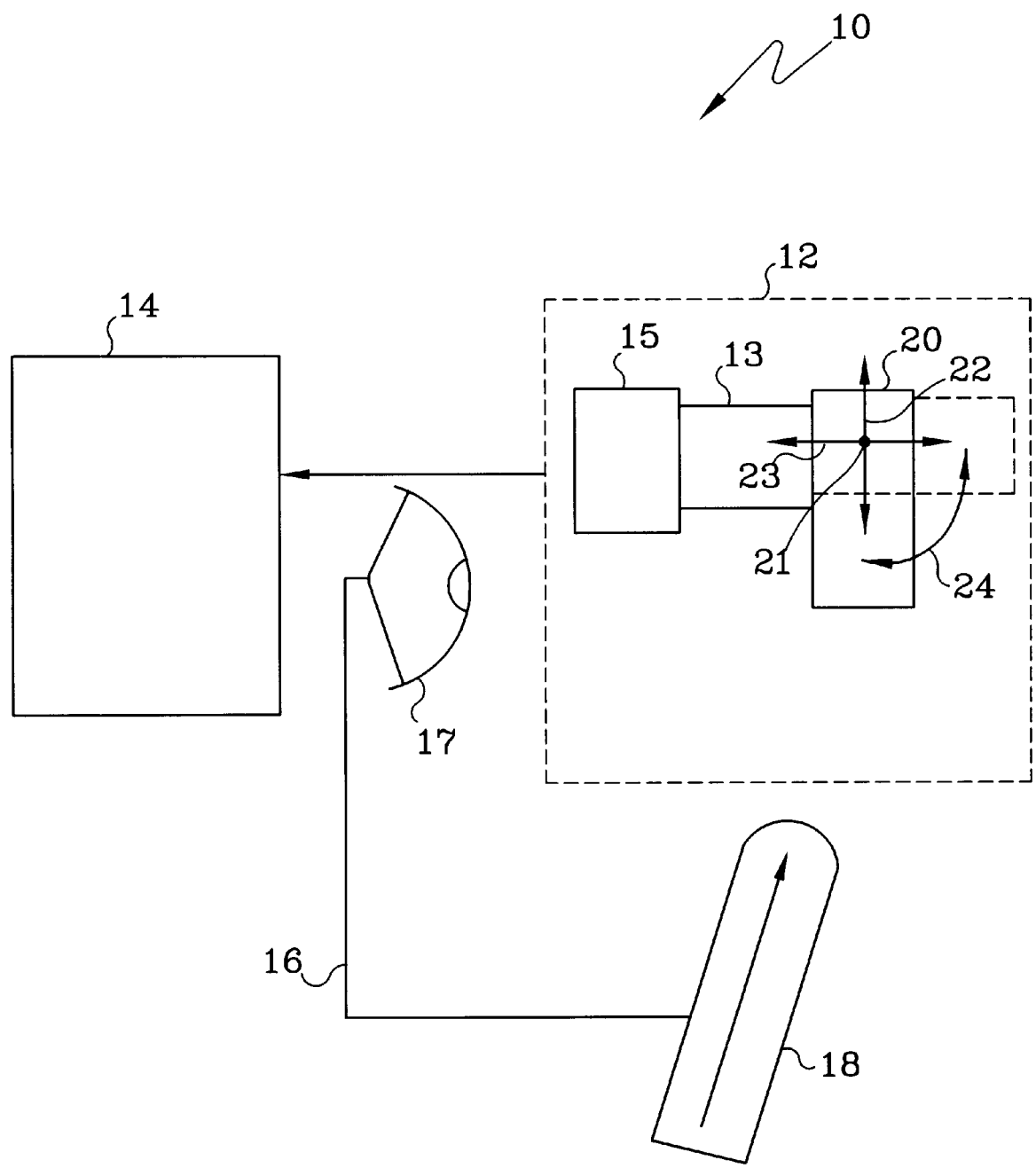
FIG. 1 is a block diagram of a head mounted display system in accordance with the present invention.
Figure 3:
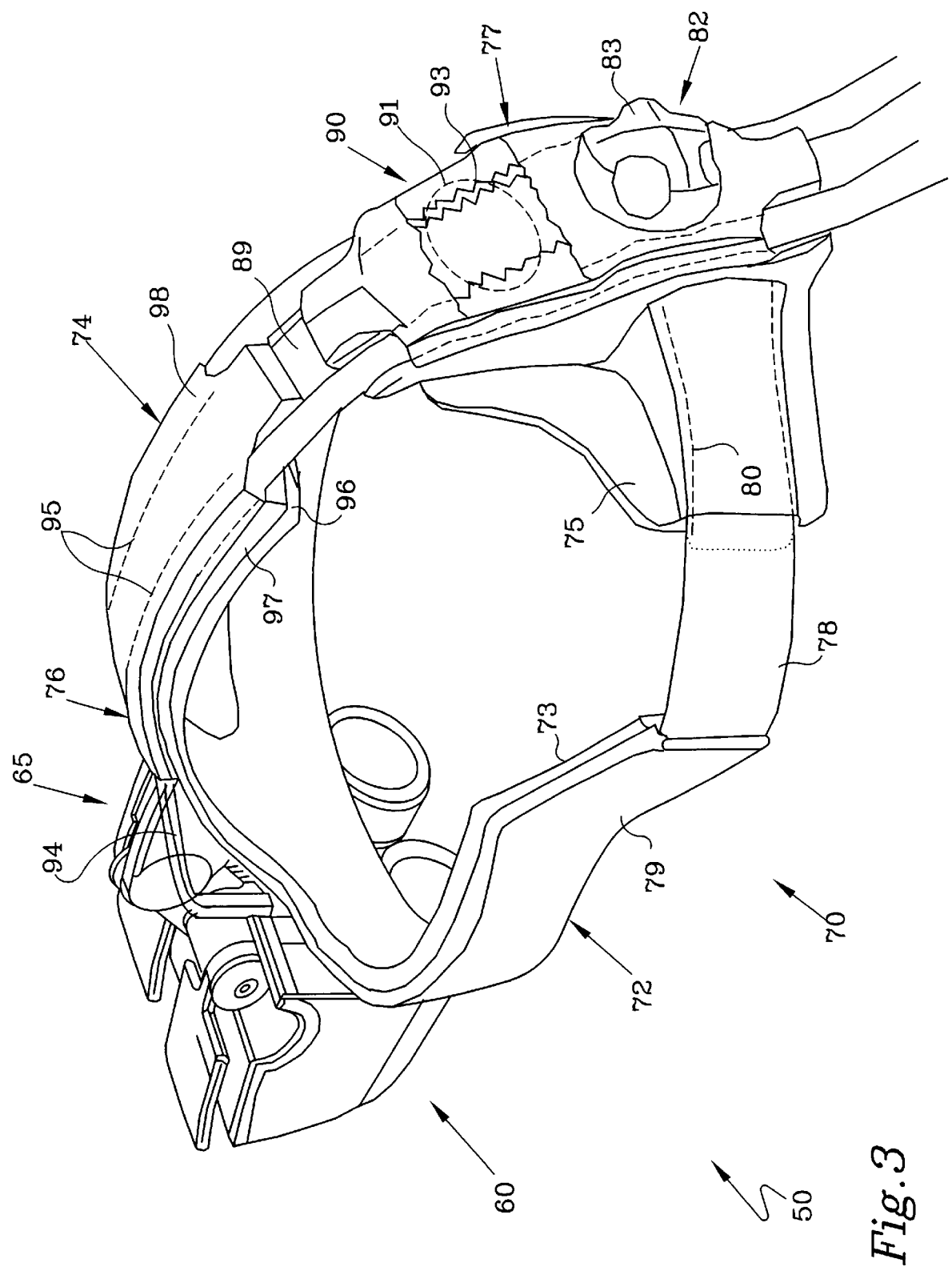
FIG. 3 is one embodiment of a head mounted display including a display and headband suspension apparatus for suspending the display at the front of the user's head.

FIG. 1 is a block diagram generally representing a head mounted display system 10 in accordance with the present invention. Head mounted display system 10 includes a head mounted display 12 electrically connected to display electronics 14. The head mounted display 12 includes a head suspension apparatus 15 for suspending a display 20 to allow viewing of images on the display 20 of head mounted display 12 by the user's eyes 17. The display 20 is mechanically connected to head suspension apparatus 15 by coupling 13. In accordance with the present invention, one embodiment of the head mounted display 12 is the head mounted display 50 including head suspension apparatus 70, coupling 65, and display 60 as shown in FIG. 3.

As shown in FIG. 1, the display 20 generally has a pivot axis 21 which is generally parallel to a plane established by the eyes 17 of the user 16 when the head mounted display 12 is suspended from the user's head. The display 20, when suspended in front of the user's head, is generally in two states, i.e., a release state and a stationary state. First, the display 20 may be in the stationary state wherein the display 20 is at a particular fixed or locked position relative to the user's eyes 17 or, in other words, relative to the head suspension apparatus 15 suspending the display 20 in front of the user's eyes 17. The display 20 may also be in the release state wherein the display 20 is freely moveable in the vertical direction, as represented generally by double ended arrow 22, and in the horizontal direction, as represented generally by double ended arrow 23. Further, in the release state, the display 20 is freely rotatable about pivot axis 21, as shown generally by double ended arrow 24.

The display 20 is normally in the stationary state until one or more forces are applied to the display 20 by the user, as generally represented by element and arrow 18, which may be the hand of the user, one or more fingers of the user, or some other mechanism for providing one or more forces on the display 20. Upon the application of one or more forces to the display 20, coupling 13 allows simultaneous movement vertically, horizontally, and rotationally relative to the head suspension apparatus 15 or eyes 17 of user 16. It will be readily apparent from the detailed description below with reference to illustrative embodiments of the present invention, that upon application of one or more forces to the display at a single point in time results in free movement of the display 20 vertically, horizontally, and rotationally about pivot axis 21 relative to the head suspension apparatus 15 or eyes 17.

It will also be apparent to one skilled in the art from the detailed description herein that there are various configurations for accomplishing the one-touch adjustability of display 20 in the vertical direction 22, horizontal direction 23, and rotationally about pivot axis 21. Such one-touch configurations may include the illustrative apparatus as described herein with reference to FIGS. 3–12, wherein a single squeeze point releases the display 20 from its stationary state into the release state via a slide bar and hinge mechanism and clutch mechanism with a return to the stationary state when the squeeze forces are released. However, the present invention is in no manner limited to such an illustrative embodiment. The present invention is limited only in accordance with the scope of the appended claims.

The scope of the appended claims is intended to encompass all one-touch adjustment mechanisms, including mechanisms using a coupling taking the form of multi-segment cables or tubes such as available under the trade designation LOC-LINE and SNAP-LOC from Cedarburg Industries (Eagan, Minn.). For example, in such mechanisms, the display 20 is held in its locked position by friction of the coupling between segments. In such a configuration, the user would merely grasp the display 20, move the display 20 to the desired position, and then release the display with the display locked in position due to friction. In such a case, no single actuation point for going from a stationary state to a release state is necessary, although the stationary state and release state are still present and vertical, horizontal, and rotational motion are still allowed in the release state. In addition, such friction locking couplings may take the form of a gooseneck system.

Further, for example, the one-touch adjustment mechanism may include a single actuation button whereby a lock/release device is used to transition from a stationary state to a release state, or any other mechanism which allows for a transition between such states upon actuation of a single actuation element by the user. For example, a user may push a release button or actuator which transitions the display from a stationary state to a release state wherein the display is freely moveable vertically, horizontally, and rotationally relative to the eyes 17. After the desired position is achieved, the button is released and a locked or fixed position is maintained in the stationary state.

In addition, instead of allowing for continuous vertical, horizontal and rotational motion of the display, any one of such directional movements may be implemented using discrete adjustment steps. For example, teeth may be formed in the slots of the illustrative slide bar and hinge mechanism described below to provide stopping points as the display is moved vertically and horizontally. Such discrete adjustment may also be facilitated by use of indents on or relative to various structures. For example, indents on the shaft of the display about which the display is rotated may provide such discrete adjustment.

Figure 2:
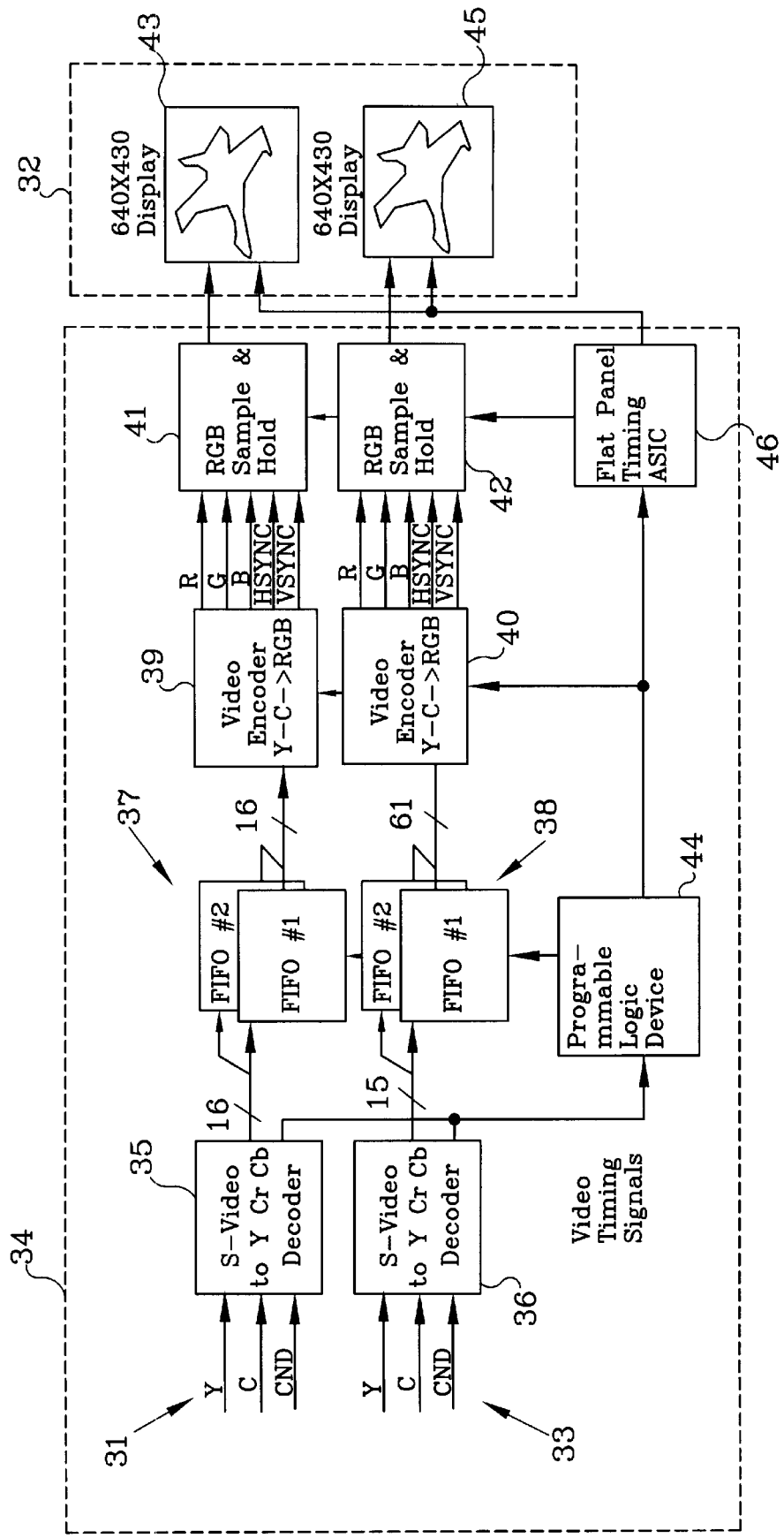
FIGS. 2 is a block diagram of one illustrative embodiment of the head mounted display system of FIG. 1.

One illustrative embodiment of the display system shown in FIG. 1 is display system 30 including a head mounted display 32 and display electronics 34, as shown in FIG. 2. The head mounted display 32, as represented generally by the dashed box, includes left and right image sources 43, 45. Such image sources may be Sony LCX 007 BK image sources, Sony Trinitron™ image sources, or any other image sources for providing images to the user 16. For example, the Sony LCX 007 BK image sources are full-color, polysilicon active matrix liquid crystal displays (AMLCD).

It should be readily apparent to one skilled in the art that the left and right image sources 43, 45 provide a binocular-type or stereo-type system when a stereo video signal, e.g., two separate video sources, are applied to the display electronics 34. However, the present invention is beneficial not only for such binocular-type systems but for any type of system. For example, the system 30 may include a video splitter for applying a single video source to both channels of the display electronics to provide a biocular system. Further, the present invention can be used with monocular systems as well.

The binocular-type display system 30 can be used for boroscope surgery and diagnostic applications and may be configured to take advantage of the availability of stereoscopic endoscopes. The type of video source used, whether single channel (two-dimensional) or stereo (three-dimensional), dictates how the display electronics 34 are utilized therewith. In the embodiment shown in FIG. 2, the display electronics 34 includes left channel electronics 31 and right channel electronics 33 controlled by programmable logic device 44 and flat panel timing circuitry 46. The left channel electronics 31 includes a decoder 35 for decoding the video signal from a video signal source, such as a stereoscopic endoscope, and also includes buffers 37, video encoder 39, and sample and hold circuit 41 for driving image source 43. Likewise, right channel electronics 33 includes decoder 36, buffers 38, video encoder 40, and sample and hold circuit 42 for driving image source 45. As indicated previously, the display electronics used in the head mounted display system 30 will vary depending primarily upon the video sources used, and will vary in part on the image sources used and the applications and specifications of the particular system with which the head mounted display is used.

FIG. 3 shows one physical illustrative embodiment of the head mounted display 12. As shown in FIG. 3, head mounted display 50 includes display 60, head suspension apparatus 70, and coupling 65 which couples display 60 to head suspension apparatus 70. Head suspension apparatus 70, or headband, is a low-weight, well-balanced headband. The head suspension apparatus 70 includes temporal support member 72 and crown support member 74. The support members 72, 74 distribute the head mounted display's weight across the crown of the head while gripping the circumference of the head for lateral stability. A large padded rear locking support portion 75 grabs the rear of the head just below the occipital lobe to provide exceptional stability and locking of the head suspension apparatus under the base of the head so as to prevent movement of the apparatus when the head is tilted, e.g., titled forward such as when a user moves her head from upright to a forward position. All surfaces of the headband in contact with the head are well-padded and of a large enough breadth to comfortably distribute compression forces.

The temporal support member 72 extends substantially entirely around the circumference of the head. The crown support member 74 includes a first end 76 and a second end 77. The first end 76 is connected to temporal support member 72 at the front of the user's head, and the second end 77 of the crown support member 74 is connected to the temporal support member 72 at the rear of the user's head.

The temporal support member 72 includes traveling section 78 proximate the rear portion 75 of temporal support member 72. The rear support portion 75 includes a channel 80 therein for accepting the traveling section 78 as the size of the temporal support 72 is adjusted utilizing circumference adjustment mechanism 82. Circumference adjustment mechanism 82 includes a circumference adjustment knob 83 operable in conjunction with a ratchet element much like that described below with regard to the crown adjustment mechanism 90 to move traveling section 78 into and out of channel 80 and lock the traveling section 78 into a position. It will be readily apparent to one skilled in the art that a substantially identical traveling section and channel are used on the right rear of the temporal support member 72.

Crown support member 74 includes a traveling section 89 which is adjustable by crown adjustment mechanism 90, shown in FIG. 3 with a crown adjustment knob removed. The crown adjustment knob is represented generally by the dotted circular structure 91. The crown adjustment mechanism 90 includes a ratchet region 93 operable with the crown adjustment knob 91 to move and lock traveling section 89 into a particular position adjusting the size of crown support member 74 to fit the user's head.

Both the crown adjustment knob and temporal adjustment knob are positioned at the rear of the user's head proximate the rear support portion 75 and the second end of the crown support 77. The placement of both the adjustment mechanisms 82, 90 together at the rear of the user's head facilitates adjustment of the head suspension apparatus 70 by the user.

It will be readily apparent that both the circumference adjustment mechanism 82 and the crown adjustment mechanism 90 may be any method utilized for adjusting the length of an element including ratchet mechanisms, slide and lock mechanisms, friction mechanisms, etc. The present invention is in no manner limited to any particular adjustment mechanism for adjusting the size of the temporal support member 72 or the crown support member 74.

In accordance with the present invention, crown support member 74 further includes cable channels 95 on the respective sides of the crown support member 74. The cable channels 95 are for receiving cables 94 used for electrically connecting the display electronics to the image sources of display 60. The cable channels 95 are represented generally by dotted lines in the crown support member 74. By routing the cables 94 through the crown support 74, service loops can be avoided at the sides of display 60. The cables 94 are mechanically attached only in the display modules of the display 60 such that appropriate stress relief is provided. The cables 94 are freely movable in the channels 95. Such a configuration frees the field of view from distracting matters and keeps the cables from snagging on equipment in the surgical field.

Preferably, the cables 94 are shielded round bundles which slide easier than many other types of cable. However, the present invention is in no manner limited to any particular size, shape, or configuration of cable. For example, the cable 94 may be flat cable.

As is further shown in FIG. 3, the crown support member 74 is made of multiple pliable layers both for support and comfort. No inner and separate suspension system is necessary for the apparatus 70 because the temporal and crown supports provide the necessary suspension conforming to the head of the user. Both the crown support member 74 and the temporal support member 72 are formed of a plurality of pliable layers. The plurality of pliable layers increases in rigidity from a pliable inner layer proximate the head to a pliable outer layer. Crown support member 74 includes a cushion layer 96, a support layer 97 of more dense material, and a pliable channel layer 98 of yet more dense material in which the cable channels 95 are defined. At least the outer layer 98 of the crown support member 74 is slidable relative to the layer 97 as the head suspension apparatus 70 is adjusted. This allows for the conformability of the head suspension apparatus to the user's head. Further, the temporal support member 72 includes a cushion layer 73 and a support layer 79 of more dense material. The cushioned layers next to the user's head may be formed of a foam that conforms to heat, removing forces and pressure points on the head. For example, one foam material which may be used is available under the trade designation ISOLOSS CF-47-SO from E-A-R Specialty Composites Corp. (Indianapolis, Ind.).

It will be apparent to one skilled in the art that portions of the crown support member 74 and the temporal support member 72 may be formed of integral or continuous material, e.g., layers thereof. For example, the cushioned layer 96 of crown support member 74 and the cushioned layer 73 of temporal support member 72 may be one continuous structure. Further, it will be apparent to one skilled in the art that the head suspension apparatus, may be of various sizes, shapes, configurations, and that various other head suspension apparatus or headbands, e.g., helmets, may be used to suspend the display 60 in front of the user's head. The transition between the stationary state of the display 60 and the release state of the display 60, as described with respect to FIG. 3 and, generally with reference to FIG. 1, is substantially unaffected by the type of head suspension apparatus used.

Therefore, any particular head suspension apparatus or headband may be used for suspending such a display.

Figure 4:
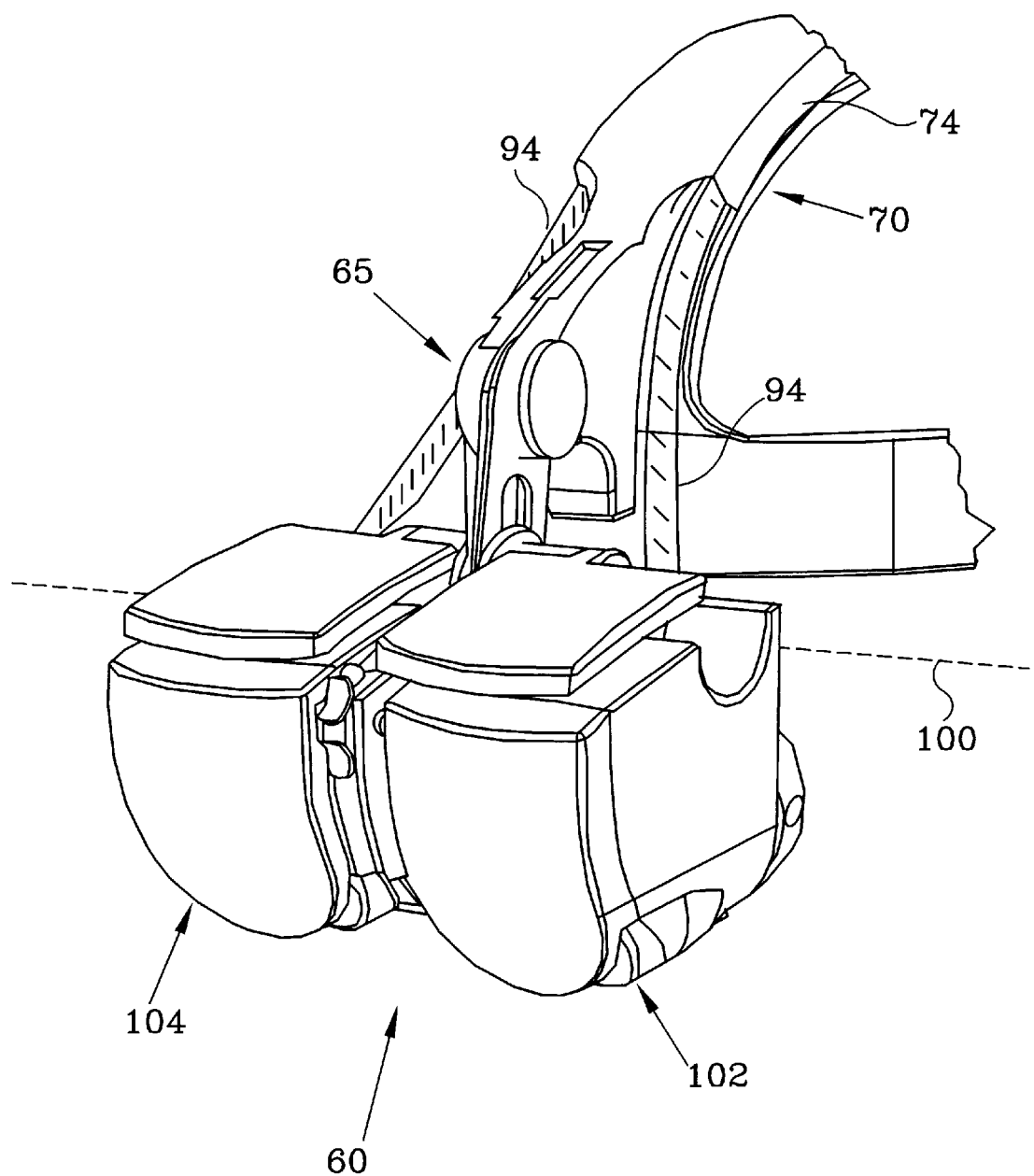
FIG. 4 is a frontal perspective view of the display of FIG. 3.

The display 60 is shown in a front perspective view in FIG. 4. The display 60 includes a left display module 102 and a right display module 104 mechanically coupled to one another and positioned along pivot axis 100 of display 60. The left and right display modules 102, 104 are electrically connected when operational to display electronics via cables 94 routed to the left and right display modules 102, 104 via crown support 74 of head suspension apparatus 70.

Figure 5:
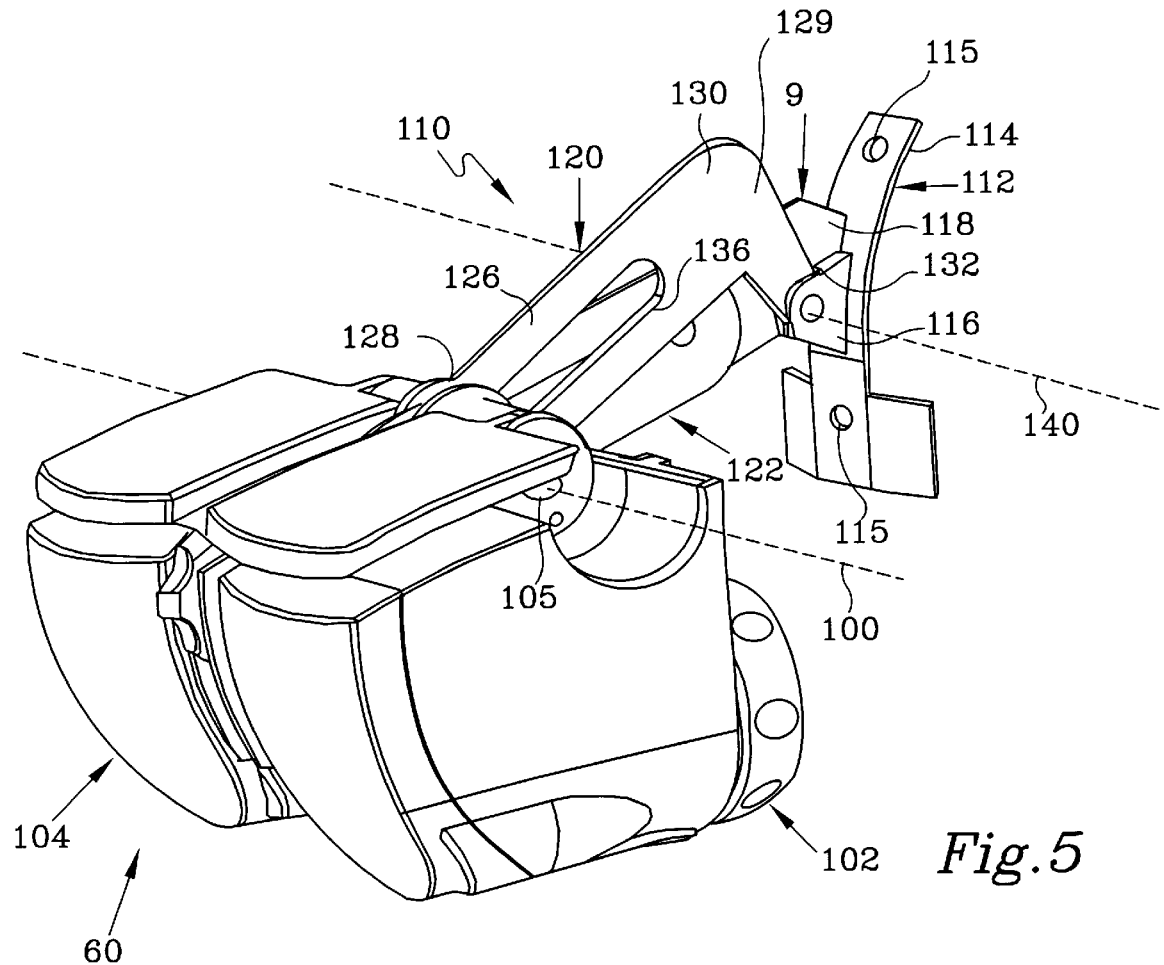
FIG. 5 is a frontal perspective view of the display of FIG. 3 cut-away at the slide bar and hinge mechanism coupling the display to the head suspension apparatus.

Coupling 65 of the head mounted display 50 used to couple display 60 to the head suspension apparatus 70 shall be described with reference to FIGS. 5–9. FIG. 5 shows display 60 in a front perspective view with the aesthetic coverings of coupling 65 removed to show a slide bar and hinge mechanism 110. The slide bar and hinge mechanism 110 is mechanically connected to head suspension apparatus 70 via plate structure 112 of the mechanism 110 and is mechanically connected to shaft 105 of display 60.

As shown in FIGS. 5–9, plate structure 112 includes a base member 114 sized for structurally supporting the display 60 by the head suspension apparatus 70. The openings 115 are for connection of the base member 114 within the head suspension apparatus 70. The plate structure 112 further includes a rigid hinge member 119 including a first hinge point portion 116 and a second hinge point portion 118, each projecting from the base member 114. The second hinge point portion 118 extends further from the base member 114 than the first hinge point portion 116. Each of the hinge point portions 116, 118 function to provide a hinge pinpoint for other members of the slide bar and hinge mechanism 110. The rigid hinge member 119 may be of various configurations as long as it provides two hinge pinpoints spaced apart from one another. The display 60 includes shaft 105 extending along pivot axis 100 at least in part for supporting other portions of display 60 and mechanically coupling left display module 102 and right display module 104.

Figure 7:
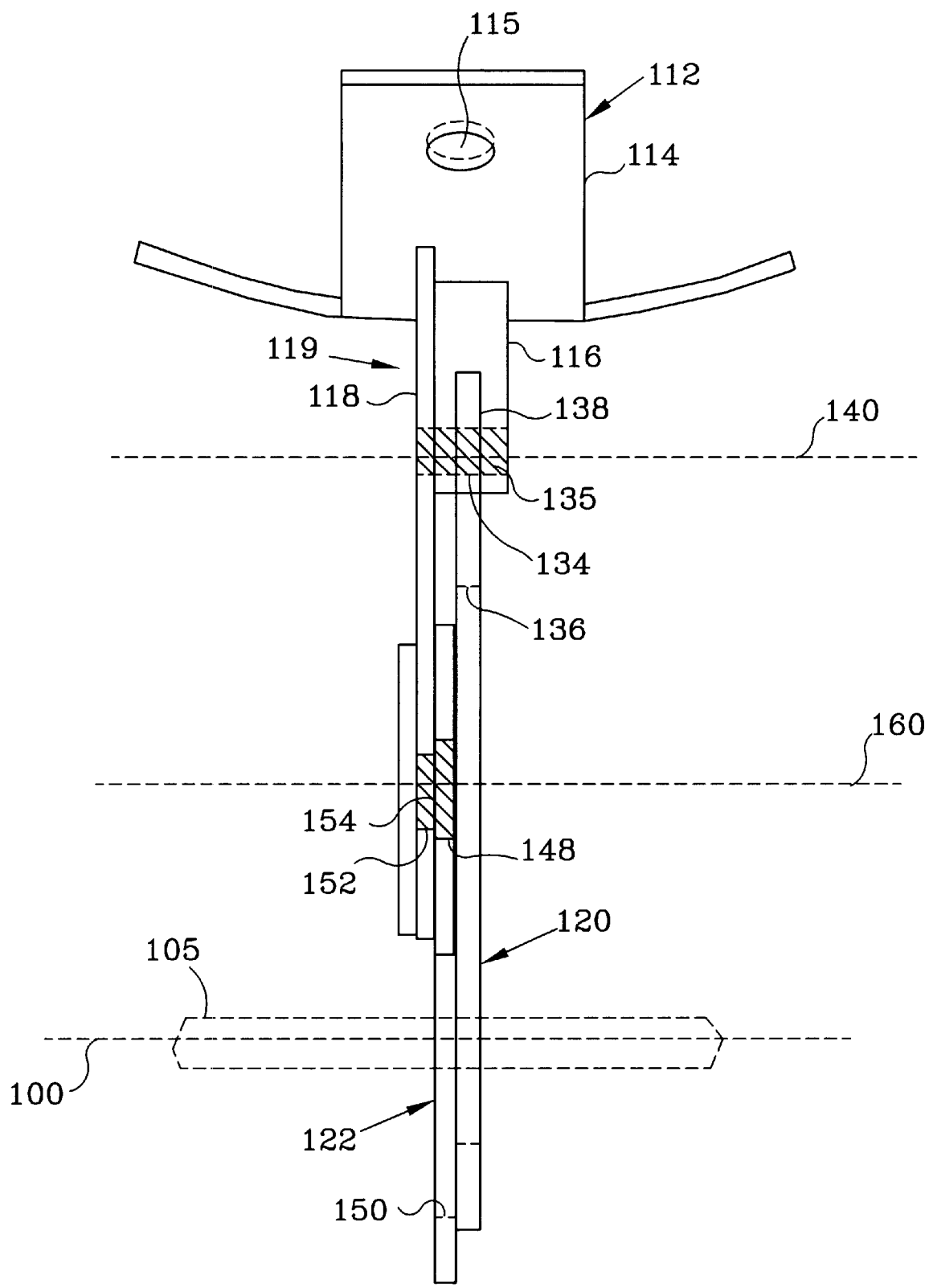
FIG. 7 is a detailed top view of the slide bar and hinge mechanism shown in FIGS. 5 and 6.

The slide bar and hinge mechanism 110 includes three members, the rigid hinge member 119 of plate structure 112, and two slotted members, namely L-shaped slotted member 120 and a substantially straight slotted member 122. The L-shaped slotted member 120 includes a first straight section 126 having a first end 128 and a second end 130. The L-shaped slotted member 120 further includes a second section 129 extending substantially orthogonal to the first section 126 and terminating at an end 132 wherein a pin opening 134 (FIG. 7) is defined. The straight section 126 of the L-shaped slotted member 120 includes a slot opening 136 extending a certain predetermined distance in the straight section 126 of L-shaped slotted member 120. The end 132 of section 129 of L-shaped slotted member 120 is sized for insertion into channel 138 which is defined in the first hinge point portion 116 (FIG. 7). Pin opening 134 in end 132 of the L-shaped slotted member 120 is pinned in receiving channel 138 and opening 133 defined through both first and second hinge point portions 116, 118 using pin 135 for allowing rotation of the L-shaped slotted member 120 about axis 140 which is parallel to axis 100 of display 60. The slot opening 136 defined in the L-shaped slotted member 120 has shaft 105 of display 60 running therethrough. With the pivot connection at the rigid hinge member 119 using pin 135 and with the shaft inserted in slot opening 136, the display 60 is mechanically coupled to the head suspension apparatus 70.

The display 60 is further coupled to the head suspension apparatus 70 using straight slotted member 122. Straight slotted member 122 has a first end 144 and a second end 146. A pin opening 148 (FIG. 7) is defined at the first end 144 of the straight slotted member 122. A slot opening 150 is defined at the second end 146 of the slotted member 122. The straight slotted member 122 is pinned to second hinge portion 118 of plate structure 112 at opening 152 defined by the second hinge portion 118 using pin 154. Inserted into slot 150 of slotted member 122 is shaft 105 of display 60. The slots 136, 150 are shown in FIG. 7 by the dashed lines at the respective ends of slotted members 120, 122. Shown extending through such slots 150, 136 is a dashed representation of shaft 105. The slots 150, 136 may be of various lengths depending on the range of motion desired for display 60.

Figure 8:
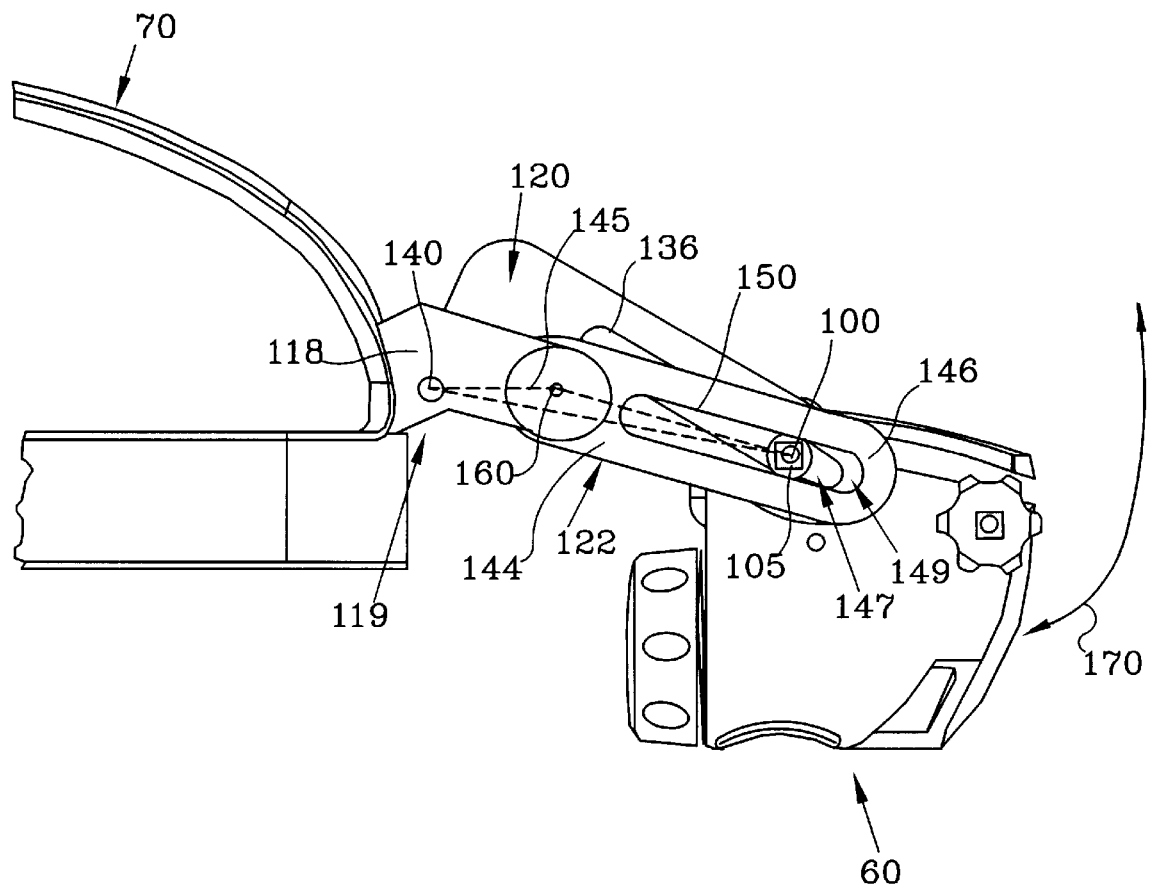
FIG. 8 is a side view of the head mounted display of FIG. 3 with the display fixed in an upward position relative to the eyes of the user with a right display module of the display removed.
Figure 9:
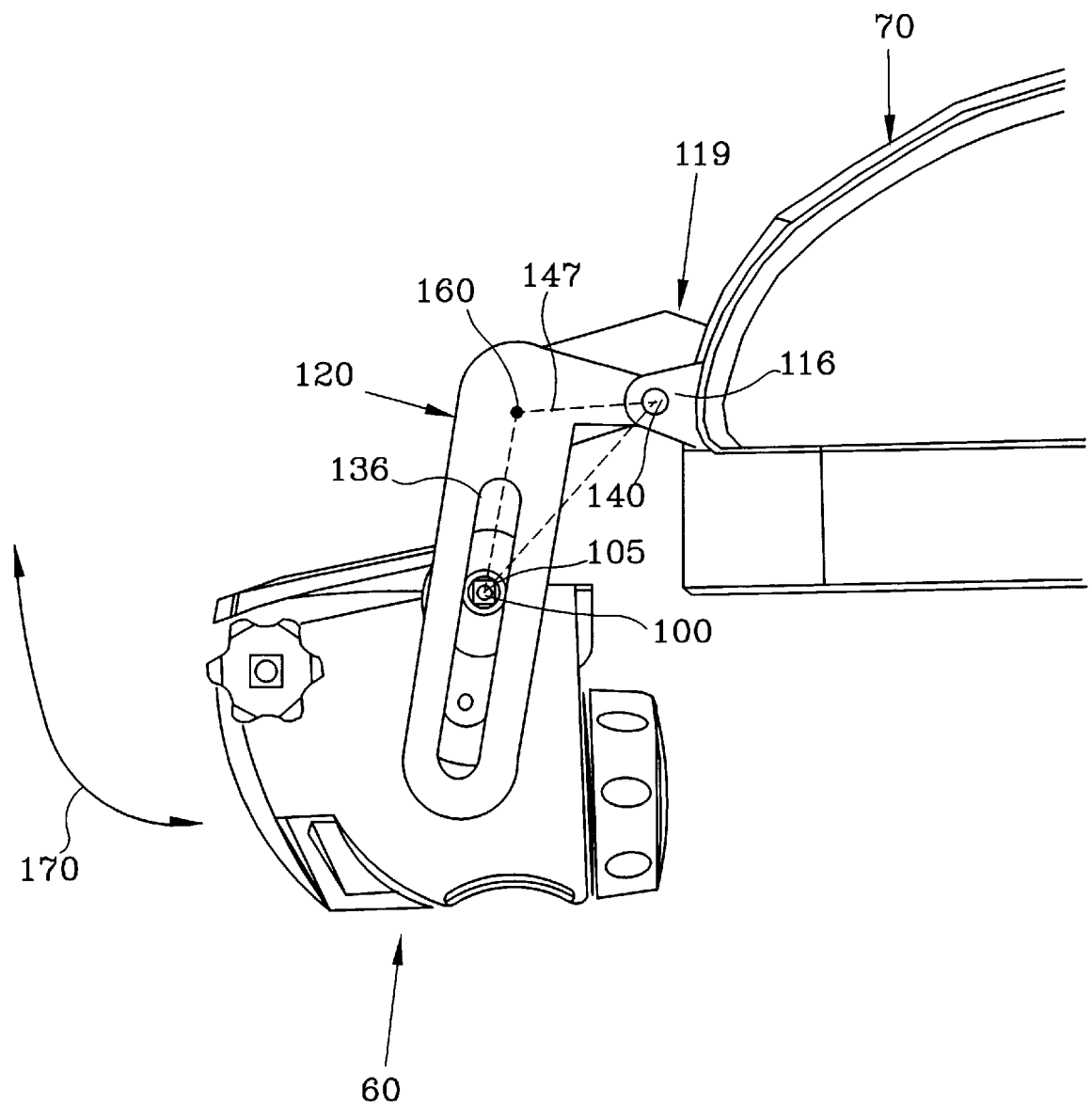
FIG. 9 is a side view of the head mounted display of FIG. 3 with the display at a downward position relative to the eyes of the user with a left display module of the display removed.

As shown in FIGS. 8 and 9, with the L-shaped slotted member 120 rotatably coupled to the head suspension apparatus 70 at axis 140, the straight slotted member 122 rotatably coupled to head suspension apparatus 70 at axis 160 and shaft 105 slidably moveable and rotatable within both slot openings 150, 136, the display 60 (e.g., when grasped by a user) is freely moveable (i.e., in a release state) into various positions. The display 60 is shown in side view at an upward position in FIG. 8 with right display module 104 removed. The display 60 is at a position above the eyes of a user. As shown therein, shaft 105 is substantially at the far ends 147, 149 of respective slots 136, 150.

The display 60 is in a downward position in FIG. 9 with left display module 102 removed. Note that the slotted member 122 is substantially hidden behind L-shaped slotted member 120 in this position with shaft 105 positioned somewhere between the ends of slots 136, 150. In a release state, the display may be rotated about axis 100, as represented generally by double ended arrow 170, in addition to being moved vertically and horizontally into the various positions.

Although the above described slide bar and hinge mechanism 110 is a preferred embodiment of the coupling 65 of the present invention, the slide bar and hinge mechanism may be implemented by any mechanism which forms a rigid triangular structure when the display is in the stationary state or locked into a particular position. For example, as shown in FIGS. 8 and 9, when the display is moved into the upward position (FIG. 8) triangular structure 145 (dashed line triangle) is formed. The triangular structure 145 has three points, two fixed hinge points at axis 140 and axis 160, and the point within slots 150, 136 at axis 100. The point within slots 150, 136 at axis 100 is movable in the release state but in the stationary state becomes locked into position to form the triangular structure 145. The other two hinge points at axis 140 and axis 160 are fixed in position and form one side of the triangular structure 145. The side of the triangular structure 145 formed between the two fixed hinge points is always of a fixed certain length. The other two sides of the triangular structure 145 vary depending upon the position of the shaft 105, and thus axis 100, within the slots 150, 136.

Triangular structure 147 is formed when the display is in the downward position as shown in FIG. 9. Triangular structure 147 includes the fixed hinge points at axis 140 and axis 160 with the side formed therebetween still of the certain fixed length. However, with the shaft 105, and thus axis 100, positioned differently in slots 150, 136, the other sides of the triangular structure 147 are of different length than the same sides of the triangular structure 145 shown in FIG. 8.

One skilled in the art will recognize that any slide bar and hinge mechanism may be used which forms a rigid triangular structure in the locked or stationary state. Further, such a triangular structure in the stationary state has rigid body members connecting all of its points so as to rigidly couple the display to the head suspension apparatus. In addition, in the release state, the slide bar and hinge mechanism includes two fixed hinge points and a movable point. In other words, the slide bar and hinge mechanism in the release state includes one fixed length between two hinge points of the triangular structure with the other two sides of the triangular structure being adjustable.

Further, one skilled in the art will recognize that other structures allowing for adjustable sides of the triangular structure may be used. For example, as opposed to slotted members, telescoping rods or any other adjustable structure may be used to allow movement of the single movable point of the triangular structure (or in other words adjust the length of the two adjustable sides of the triangular structure).

Yet further, one skilled in the art will recognize that depending upon the various configurations and dimensions of the slide bar and hinge mechanism, that various degrees of freedom of movement of the display 60 can be achieved. For example, the slotted members may have curved sections as opposed to straight sections and still allow for the desired range of movement for the display.

In the configuration described above, display 60 can be moved vertically, horizontally, and rotationally relative to head suspension apparatus 70 when the display 60 is in a release state or, in other words, such movement is possible when, upon a single touch of the user, a clamping structure locking the slide bar and hinge mechanism 110 in a particular position is released. As such, the display 60 is normally in a locked position until released. Although various clamping structures may be used to provide for locking of the slide bar and hinge mechanism 110 to achieve a stationary state for the display 60, one particular illustrative embodiment using a clutch mechanism shall be described with reference to FIGS. 10 and 11A–11D in addition to description of other particular details with regard to display 60. One skilled in the art will recognize that any clutch mechanism which allows for the engagement and disengagement of a clamping or sandwiching structure locking the display 60 in a particular position and releasing the display 60 and which is operable with a single applied touch by the user, e.g., squeeze of a paddle towards a portion of the display, may be used according to the present invention. As such, the present invention is not limited to the illustrative clutch mechanism described herein.

Figure 10:
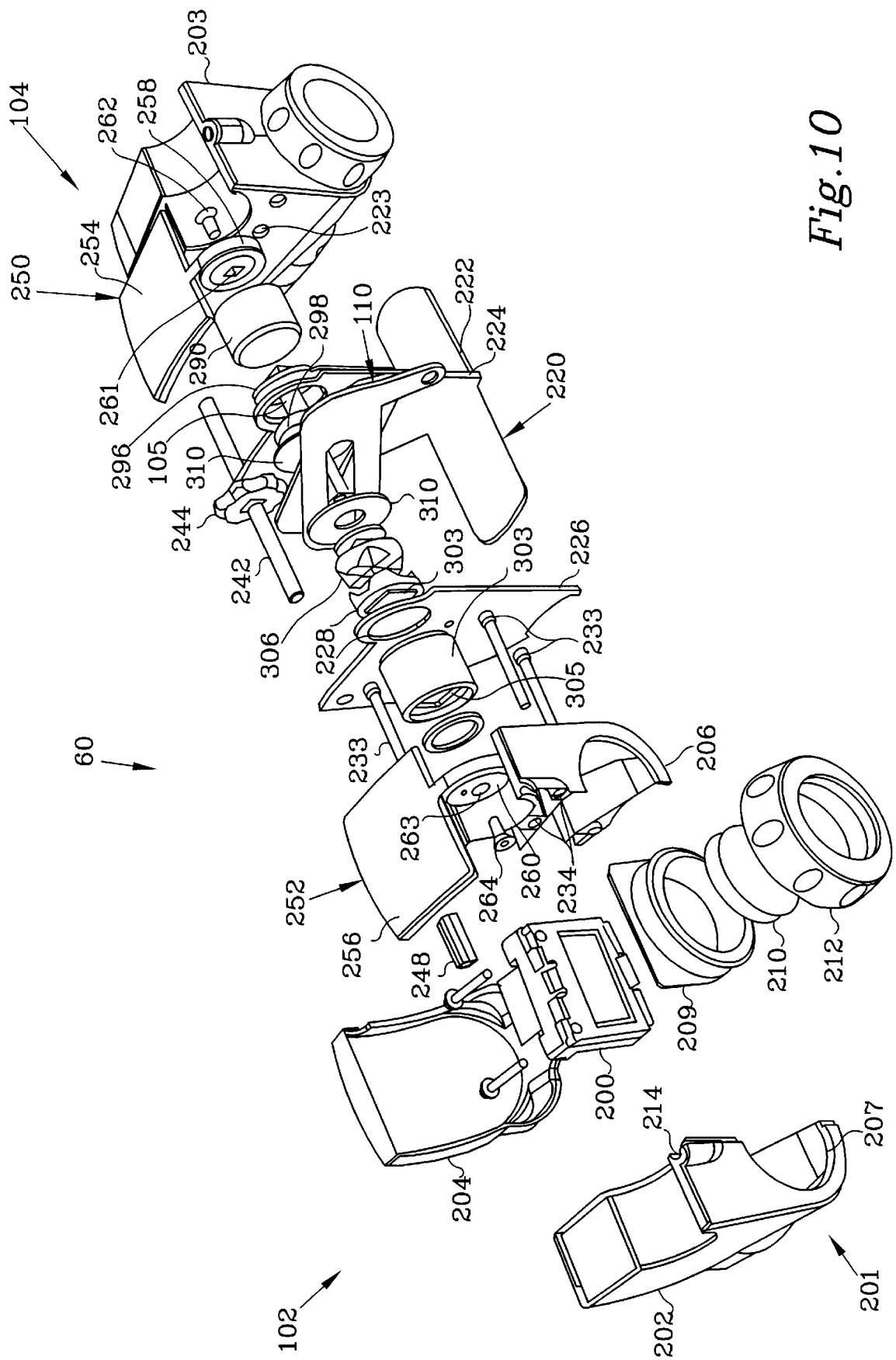
FIG. 10 is an exploded view of the display shown in FIG. 3.
Figure 11:
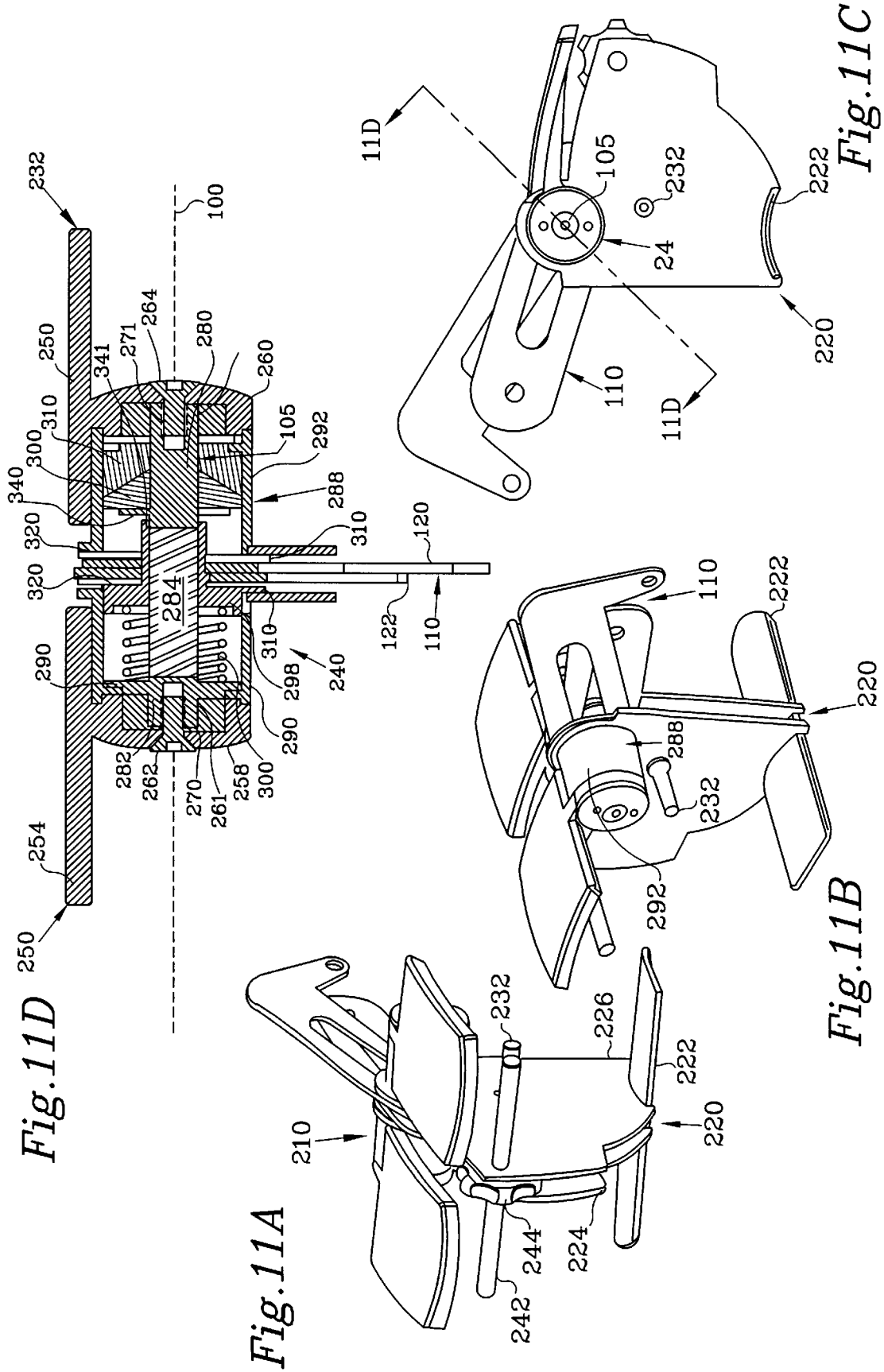
FIGS. 11A–11D include a front perspective view, a rear perspective view, a side view, and a cross-section view at line 11D—11D of FIG. 11C, respectively, of the clutch mechanism and portions of the slide bar and hinge mechanism of the display shown in FIG. 3 in accordance with the present invention.

The display 60, as shown in the perspective view of FIG. 10, includes the left display module 102, shown in exploded view, and an assembled right display module 104. Left and right display modules 102, 104 include substantially symmetrical elements and therefore the elements of left display module 102 shall only be described for simplicity purposes. Left display module 102 includes image source 200 positioned within a display housing 201 formed of a first side housing member 202, a second side housing member 206, and a rear housing member 204. Such housing members may snap-fit together or be connected by any suitable fasteners, such as the housing screw fasteners 233 and inserts 234 (as shown in FIG. 10, left display module 102) for holding first and second side housing members 202, 206 together. The housing 201 includes an opening 207 defined opposite the rear housing member 204 for receiving a lens holder 209 for placement of lens 210 and upon which focus ring 212 is mounted. As such, the image source 200 is viewable through the lens 210 by the user. The routing of cable for the electrical connection of image source 200 to display electronics is provided through cable opening 214.

The display 60 further includes a center structure 220 to which the left and right display modules 102, 104 are mechanically connected. The center structure 220 includes a thumb indent base member 222 and two center plates 224, 226 extending substantially orthogonal to the thumb indent base member 222. At the upper section of each of the center plates 224, 226 are defined openings 230, 228, respectively, through which shaft 105 and associated elements of clutch mechanism 240 (FIG. 11) are inserted. The center plates 224, 226 include pins 232 (FIG. 11) upon which the left and right display modules 102, 104 ride. For example, the pins 232 ride in openings 223 (as shown in FIG. 10, right display housing 203).

The left and right display modules 102, 104 are movably mounted for lateral movement of the display modules 102, 104 to increase and decrease the distance therebetween so as to allow for adjustment of interpupillary distance (IPD). The structure for allowing adjustment of the interpupillary distance includes a threaded rod 242 having a finger adjustment knob 244 positioned substantially at the center of the rod 242 as shown in FIGS. 10 and 11A–11C. The finger adjustment knob 244 is positioned between center plates 224, 226 with the one end of the threaded rod 242 extending through plate 224 and a second end of the threaded rod extending through center plate 226. Within the housing 201 of the display module 102 (and, thus, also display module 104), a threaded insert 248 is connected onto respective ends of threaded rod 242. With the left display module 102 and right display module 104 riding on the pins 232 projecting from center plates 224, 226, the lead screw structure described above allows for a user to turn the finger adjustment knob 244 to increase or decrease the distance between the left and right display modules 102, 104. The adjustment of interpupillary distance is completely separate from the clutch mechanism 240, to be described further below, which provides the ability to release the display from its stationary state (e.g., a locked slide bar and hinge mechanism) such that the entire display is freely moveable vertically, horizontally, and rotationally relative to the eyes of the user.

The clutch mechanism 240 is shown in the cross-sectional view of FIG. 11D in a stationary state or, in other words, in a state wherein the display 60 is in a locked position relative to the head suspension apparatus 70. The clutch mechanism 240 includes two paddle members 250, 252 i.e., levers. Each paddle member 250, 252 includes a paddle section 254, 256 and a circular end section 258, 260, respectively. In each of the circular end sections 258, 260 are defined holes 261, 263 for insertion of threaded screws 262, 264. Threaded screws 262, 264 are sized for insertion and mechanical coupling into respective threaded insert sections 270, 271 of shaft 105. Such construction of end sections 258, 260 relative to shaft 105 holds the clutch mechanism 240 together with shaft 105 solidly linking paddle section 250 to paddle section 252.

Shaft 105 includes three sections. A first end section 280, which is of a square cross-section, and an opposing second end section 282, which is also of a square cross-section (i.e., square cross-section taken in a plane orthogonal to axis 100). A round cross-section 284 exists between the two end sections 280, 282. Circular end sections 258, 260 are keyed in a square shape for accepting the first and second end sections 282, 280 of shaft 105, respectively. As described above, therefore, the paddle sections 250, 252 are solidly linked to one another through shaft 105, and movement of paddle 250 moves paddle 252, and vice-versa.

Provided between the two circular end sections 258, 260 are numerous clutch elements. Surrounding these clutch elements is clutch housing 288 which is of a substantially cylindrical configuration. The housing 288 includes two cylindrical members 290, 292 positioned on respective sides of center plates 224, 226 of center structure 220.

As shown in FIGS. 10 and 11D, the various clutch mechanism elements include shaft 105, as previously described, and which further includes an annular lip section 296 extending substantially orthogonally from the end section 282 of shaft 105. Positioned concentric with respect to shaft 105 is clutch plate 298. A compression spring 300 also concentric with shaft 105 extends between and in contact with lip section 296 of shaft 105 and an indent of clutch plate 298. Further positioned concentric with shaft 105 is an annular fixed cam portion 302. Fixed cam portion 302 is fixed and does not move within housing section 292 as fixed cam 302 includes a square keying structure 303 sized for locking in the square defined opening 305 of housing section 292. Adjacent fixed cam portion 302 is moveable cam portion 306 which includes a square opening therethrough keyed for accepting the square end section 280 of shaft 105. Thus, cam portion 306 rotates with shaft 105 when shaft 105 is rotated, i.e., by movement of paddles 250, 252. Fixed cam portion 302 includes an opening therethrough allowing for rotation of shaft 105 and thus also cam portion 306. The clutch mechanism 240 further includes washers 310, e.g., rubber washers, positioned on respective sides of slide bar and hinge mechanism 110 including slotted members 120, 122 for use in application of clamping forces on the slide bar and hinge mechanism 110.

Figure 6:
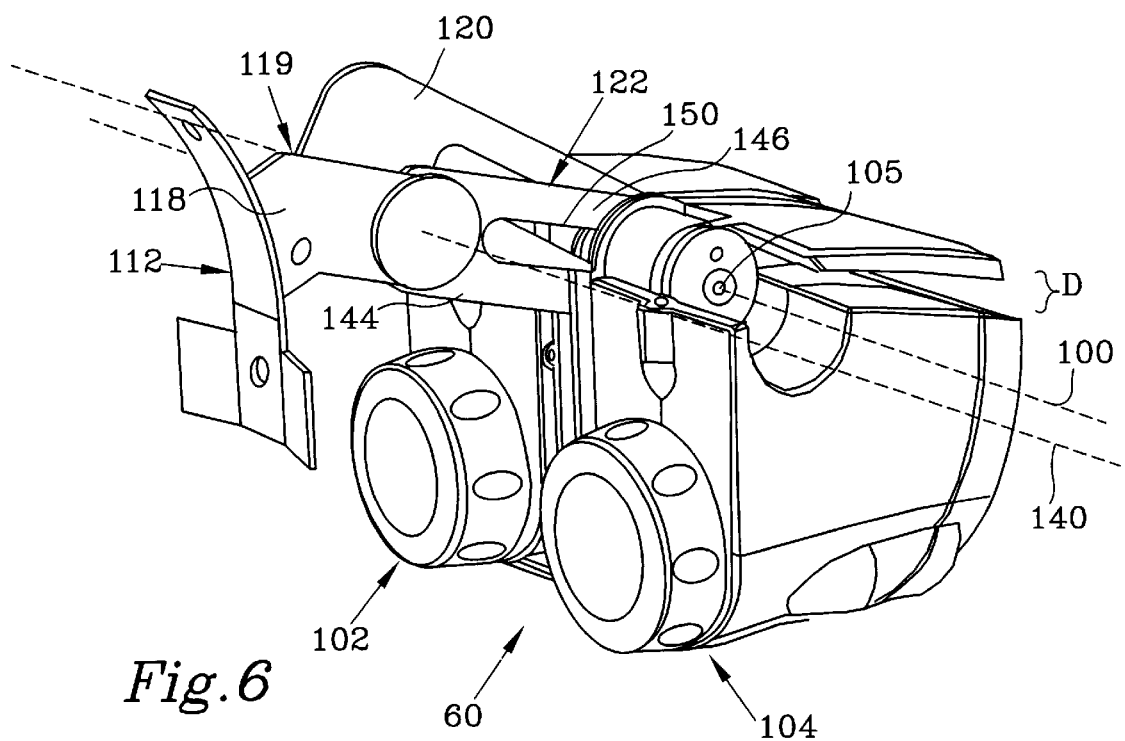
FIG. 6 is a rear perspective view of the structure shown in FIG. 5.

In operation, the clutch mechanism 240 works in the following manner. With the paddle sections 254, 256 of respective paddles 250, 252 spaced a distance from display housing 203, 201 of the right and left display modules 104, 102, as shown in FIG. 6 by distance D, the spring force of compression spring 300 (which may be any other known suitable type of spring) positioned between lip section 296 and clutch plate 298 forces annular surface 320 of clutch plate 298 against slide bar and hinge mechanism 110 via washers 310 and against annular surface 322 of housing section 292. Thus, the slide bar and hinge mechanism 110 is sandwiched therebetween and the display 60 is prevented from moving vertically, horizontally, or rotationally. This is the stationary state of the display 60 with the display 60 having a fixed or locked position relative to the head suspension apparatus 70 and is shown in FIG. 11D.

Upon movement of either paddle section 254, 256 towards housing 201 or housing 203 (decreasing distance D), the shaft 105, which is square keyed to the circular end sections 258, 260 of paddles 250, 252, rotates. With rotation of shaft 105, cam portion 306 rotates and is forced laterally by slanted surfaces of fixed cam 302 along axis 100 such that surface 340 contacts surface 341 of clutch plate 298 forcing compression of spring 300 and releasing or disengaging the sandwiching or clamping forces being applied to slide bar and hinge mechanism 110 previously applied thereto via surfaces 320, 322. In such a release state, the display 60 is freely rotatable about axis 100, as the shaft 105 includes rounded section 284 between the square end sections of shaft 105. Further, with such forces released, the display 60 is freely moveable in the vertical and horizontal directions via the sliding of shaft 105 in slots 150, 136 of the slide bar and hinge mechanism 110 along with the pivoting movement allowed at pivot axis 140, 160.

Upon release of paddles 250, 252, the clutch mechanism 240 returns to the stationary state under control of the spring force of compression spring 300. The thumb indent base member 222 provides for a position of a user's thumb such that paddles 250, 252 may be more easily moved towards one of the respective display housings. As such, a simple squeezing motion and grasping around the display releases the clamping action on the slide bar and hinge mechanism 110 providing for continuous positioning of the display 60 vertically, horizontally, and rotationally as the display 60 is grasped. Only the paddles 250, 252 and thumb indent base member 222 of center structure 220 are grasped. In other words the user never needs to touch the display housings 201, 203.

Figure 12:
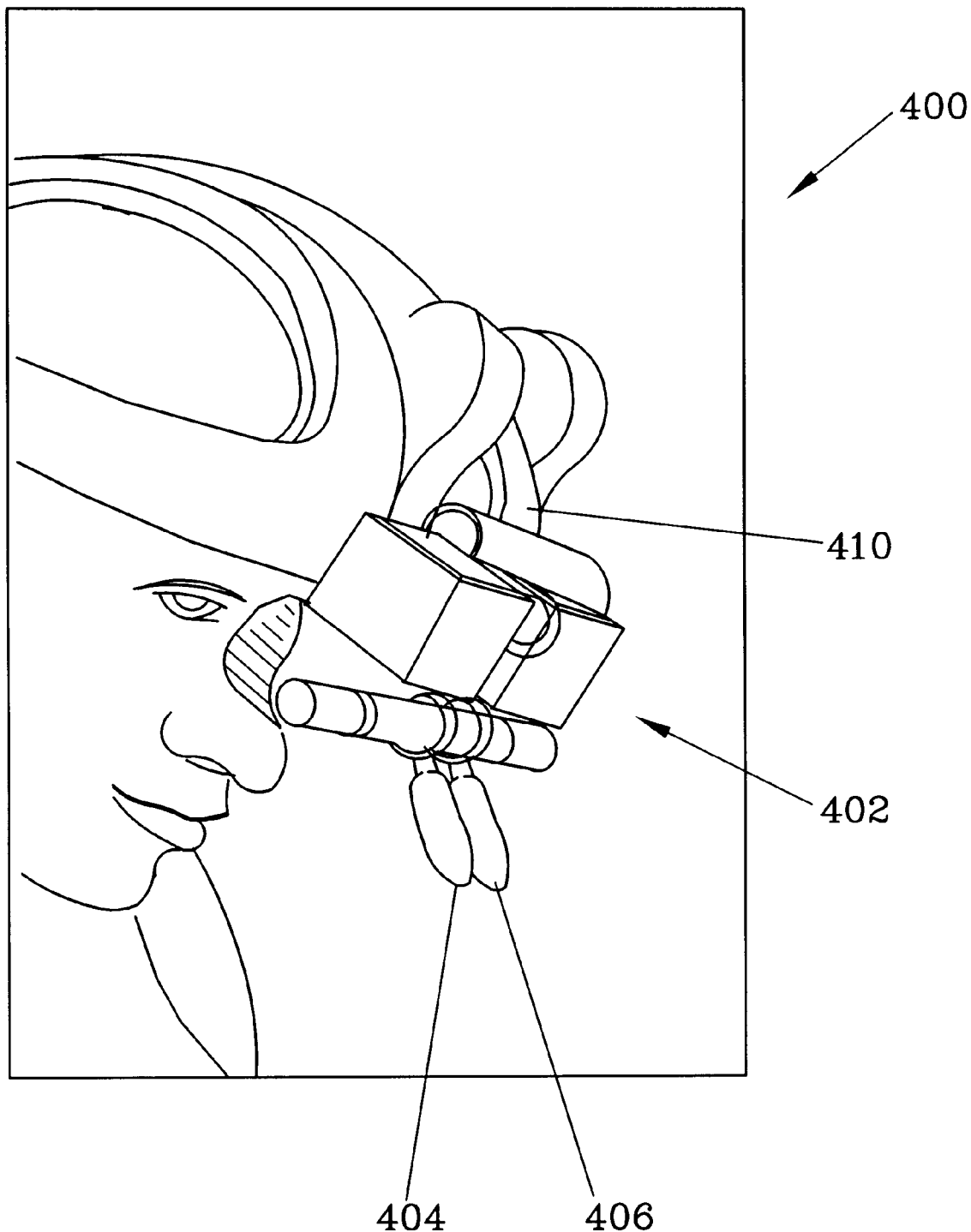
FIG. 12 is a perspective view of an alternate embodiment of the display including an alternate single actuation point.

It will be readily apparent to one skilled in the art that various mechanisms may be used to provide the necessary forces and pressure on the slide bar and hinge mechanism 110 or any other mechanism used to allow for the vertical, horizontal, and rotational motion of the display 60 relative to the head suspension apparatus 70. Further, it will be readily apparent that various actuation apparatus, e.g., paddle members 250, 252, may be used for actuating the release of the display 60 from the stationary state to the release state. For example, as shown in FIG. 12, an alternate embodiment of a head mounted display 400 is shown wherein the single touch actuation for releasing the display 402 from the stationary state to a release state is accomplished by squeezing a moveable paddle 406 relative to a fixed paddle 404. Such movement of moveable paddle 406 to fixed paddle 404 translates motion to a clutch mechanism to accomplish release of forces against a substantially similar slide bar and hinge mechanism 410. As can be seen, the slide bar and hinge mechanism 410 includes members which are similar but not identical to those of slide bar and hinge mechanism 110, showing that the size and configuration of the slide bar and hinge mechanism 110 may take various configurations so long as the fixed hinge points and adjustable point allow for movement of the display vertically, horizontally, and rotationally.

Although the present invention has been described with particular reference to illustrative embodiments thereof, variations and modifications of the present invention can be made within a contemplated scope of the following claims, as is readily known to one skilled in the art.

What is claimed is:

1. A head mounted display comprising:
   a head suspension apparatus;
   a display movable relative to the head suspension apparatus; a coupling attaching the display to the head suspension apparatus;
   a locking mechanism movable between a normally locked state and an unlocked state relative to the coupling, wherein the display is in a stationary position relative to the head suspension apparatus when the locking mechanism is in the locked state; and
   a user actuator element operably coupled to the locking mechanism to move the locking mechanism between the normally locked state and the unlocked state, wherein the display is movable in both a horizontal and vertical direction relative to the head suspension apparatus when the locking mechanism is in the unlocked state.

2. The head mounted display of claim 1, wherein the display includes at least one image source positioned along an axis thereof, and further wherein the the at least one image source is rotatable about the axis when the locking mechanism is in the unlocked state.

3. The head mounted display of claim 2, wherein the coupling includes a slide bar and hinge mechanism that forms a rigid triangular structure when the locking mechanism is in the locked state and the display is in the stationary position.

4. The head mounted display of claim 3, wherein the slide bar and hinge mechanism includes two fixed hinge points and a movable hinge point and further wherein the slide bar and hinge mechanism is movable into a plurality of triangular structures as the movable hinge point is moved relative to the two fixed hinge points when the locking mechanism is in the unlocked state.

5. The head mounted display of claim 4, wherein the slide bar and hinge mechanism includes:
   a first rigid member projecting from the head suspension apparatus;
   a second member having a first end rotatably coupled at a first fixed hinge point of the first rigid member and a second end including a slot slidingly coupled to a shaft element lying along the axis of the display such that the shaft element can move in the slot thereof when the locking mechanism is in the unlocked state; and
   a third member having a first end rotatably coupled at a second fixed hinge point of the first rigid member and a second end including a slot slidingly coupled to the shaft element such that the shaft element can move in the slot thereof when the locking mechanism is in the unlocked state.

6. The head mounted display of claim 5, wherein one of the first and second members is an L-shaped member and the other is a straight member.

7. The head mounted display of claim 1, wherein the locking mechanism and user actuator element are a clutch mechanism for disengaging and engaging a clamping structure thereof relative to the coupling.

8. The head mounted display of claim 7, wherein the display includes a display housing with the user actuator element at a normal position spaced a distance from the display housing, and further wherein the locking mechanism is released from the locked state to the unlocked state upon user movement of the user actuator element towards the display housing.

9. The head mounted display of claim 8, wherein the locking mechanism returns to the locked state upon release of the user actuator element by the user and return of the user actuator element to the normal position.

10. A head mounted display comprising:
    a display having at least one image source;
    electrical connection lines connected to the at least one image source;
    a head suspension apparatus coupled to the display, the head suspension apparatus including:

an adjustable temporal support for positioning about the circumference of a user's head, wherein the adjustable temporal support includes a temporal support member and a temporal circumference adjustment element operable to change the size of the temporal support member; and an adjustable crown support having a first end connected to a first portion of the temporal support at the front of the user's head and a second end connected to a second portion of the temporal support at the rear of the user's head, wherein the adjustable crown support includes a crown support member and a crown adjustment element operable to chance the size of the crown support member, and further wherein the adjustable crown support includes at least one channel for allowing the electrical connection lines to move freely therein, the electrical connection lines being routed from the at least one image source to the rear of the user's head through the at least one channel.

11. The head mounted display of claim 10, wherein the head suspension apparatus further includes a locking support portion proximate the second portion of the temporal support and the second end of the crown support wherein the locking support portion is of a configuration to grab a portion of the rear of the user's head to lock the head suspension apparatus on the user's head so as to prevent movement of the head suspension apparatus when the user's head is tilted.

12. The head mounted display of claim 10, wherein the crown adjustment element and the temporal circumference adjustment element for use in adjusting the size of the crown support member and the size of the temporal support member, respectively, are positioned proximate the second portion of the temporal support and the second end of the crown support.

13. The head mounted display of claim 10, wherein at least one of the crown support and the temporal support are formed of a plurality of pliable layers, the plurality of pliable layers increasing in rigidity from a pliable inner layer proximate the head to a pliable outer layer.

14. A head mounted display comprising:

a head suspension apparatus for positioning on a user's head;

a display including at least one image source positioned along an axis thereof;

means for coupling the display to the head suspension apparatus;

means for maintaining the display in a stationary state at a desired position relative to the head suspension apparatus; and means for releasing the display from the stationary state to a release state wherein the display is always freely movable vertically and horizontally relative to the head suspension apparatus and further wherein the at least one image source is freely movable rotationally about the axis of the display in the release state.

15. A head mounted display comprising:

a head suspension apparatus;

at least one image source movable relative to the head suspension apparatus;

a coupling attaching the at least one image source to the head suspension apparatus;

a clutch mechanism including a locking structure movable between a locked state and an unlocked state and an actuator element operable with the locking structure to move the locking structure between the locked and unlocked state, wherein the locking structure locks the coupling to maintain the at least one image source at a desired position relative to the head suspension apparatus, and further wherein activation of the actuator element releases the locking structure such that the at least one image source is freely moveable both vertically and horizontally relative to the head suspension apparatus.

16. The head mounted display of claim 15, wherein the head mounted display includes a display housing, wherein the at least one image source is positioned for viewing within the display housing, wherein the actuator element is at least one paddle lever spaced at a normal position at a distance from the display housing, and further wherein the locking structure is moved to the unlocked state and the at least one image source is freely moveable both vertically and horizontally relative to the head suspension apparatus upon user movement of the paddle lever towards the display housing.

17. The head mounted display of claim 16, wherein the locking structure returns to the locked state and the at least one image source is locked in a position upon release of the paddle lever by the user and return of the paddle lever to the normal position.

18. The head mounted display of claim 15, wherein the coupling includes a slide bar and hinge mechanism that forms a rigid triangular structure when the locking structure is in the locked state and locks the coupling to maintain the at least one image source in the desired position.

19. The head mounted display of claim 18, wherein the slide bar and hinge mechanism includes two fixed hinge points and a movable hinge point, and further wherein the slide bar and hinge mechanism is movable into a plurality of triangular structures as the movable hinge point is moved relative to the two fixed hinge points when the locking structure is in the unlocked state.

20. The head mounted display of claim 19, wherein the slide bar and hinge mechanism includes:

a first rigid member projecting from the head suspension apparatus;

a second member having a first end rotatably coupled at a first fixed hinge point of the first rigid member and a second end including a slot slidingly coupled to a shaft element lying along the axis of the display such that the shaft element can move in the slot thereof when the locking structure is in the unlocked state; and a third member having a first end rotatably coupled at a second fixed hinge point of the first rigid member and a second end including a slot slidingly coupled to the shaft element such that the shaft element can move in the slot thereof when the locking mechanism is in the unlocked state.

* * * * *